United States Patent [19]
Killion et al.

[11] Patent Number: 5,099,856
[45] Date of Patent: Mar. 31, 1992

[54] ELECTRODE ISOLATION AMPLIFIER

[75] Inventors: Mead C. Killion, Elk Grove Village; Donald L. Wilson, Roselle; Jonathan K. Stewart, Bensenville, all of Ill.

[73] Assignee: Etymotic Research, Inc., Elk Grove Village, Ill.

[21] Appl. No.: 433,633

[22] Filed: Nov. 8, 1989

[51] Int. Cl.$^5$ .............................................. A61B 5/04
[52] U.S. Cl. .................................. 128/731; 128/746; 128/419 R
[58] Field of Search ............... 128/731, 732, 746, 632, 128/635, 419 R, 696, 653, 901, 908; 250/215, 515.1

[56] References Cited

U.S. PATENT DOCUMENTS

| | | | |
|---|---|---|---|
| 3,794,841 | 2/1974 | Cosentino et al. | 128/908 |
| 3,896,274 | 7/1975 | Fraim et al. | 381/68 |
| 4,037,586 | 7/1977 | Grichnik | 128/731 |
| 4,539,441 | 9/1985 | Eggert et al. | 381/68 |
| 4,566,464 | 1/1986 | Piccone et al. | 128/731 |
| 4,679,002 | 7/1987 | Sherwin et al. | 128/731 |
| 4,689,819 | 8/1987 | Killion | 381/68 |
| 4,709,702 | 12/1987 | Sherwin | 128/731 |
| 4,784,144 | 1/1988 | Ono et al. | 128/634 |
| 4,967,038 | 10/1990 | Gevins et al. | 128/731 |

FOREIGN PATENT DOCUMENTS

| | | | |
|---|---|---|---|
| 8909019 | 10/1989 | PCT Int'l Appl. | 128/731 |
| 0633172 | 8/1979 | U.S.S.R. | 128/901 |

OTHER PUBLICATIONS

"Electrical Safety in Hospitals-Reduction of Leakage Currents by use of a Double Screened Mains Transformer", J. Pontoppidan et al., Bio-Med Eng. (GB), vol. 9, No. 1, Jan. 1974, 21-23.

*Primary Examiner*—Stephen C. Pellegrino
*Assistant Examiner*—Steven J. Shumaker
*Attorney, Agent, or Firm*—McAndrews, Held & Malloy, Ltd.

[57] ABSTRACT

A system for detecting and transmitting body electrical signals in the presence of ambient electrical interference that uses a transmiter circuit including an amplifier coupled to and in close proximity to two or more body electrodes, a light pulse generator that receives its input from that amplifier and provides a pulse-duration-modulated series of light pulses, and a remote receiver including a transducer which demodulates the transmitted light pulses into electrical pulses of corresponding duration and frequency and a demodulator which accepts those electrical pulses and produces an amplified replica of the original signal developed between the body electrodes, thereby effectively providing complete electrical isolation of the electrode amplifier from the remaining bioelectrical signal analysis equipment. A valuable additional feature of the invention is a complete electrostatic shield around the amplifier-transmitter as well as the electode leads, so that the small amount of residual capacitive coupling to the amplifier circuit itself is effectively shunted to the same average (body) potential as that of the electrodes.

1 Claim, 6 Drawing Sheets

ELECTRODE ISOLATION AMPLIFIER

FIELD OF THE INVENTION

This invention relates to the field of bioelectric detection generally and more specifically to low-noise, interference-resistant amplifiers adapted for accepting the signals from such electrodes and delivering amplified output signals to equipment for analyzing such signals.

BACKGROUND OF THE INVENTION

Unlike conventional hearing testing techniques which require the cooperation and participation of the subject or patient, Auditory Brainstem Response (ABR) testing senses the patient's hearing response automatically through the direct measurement of bioelectrical activity at the subject's brainstem. The use of Auditory Brainstem Response recordings has now become routine in the evaluation of hearing. They are particularly useful where difficulty would be encountered in conventional testing or where additional information is required beyond that available from conventional testing. Examples include infants who are uncooperative or are too young to respond consistently, foreign-language speaking adults, and suspected 8th nerve tumor patients. The ABR instrument provides an objective measure of the operation of the auditory system by using computer averaging to detect the small electrical potentials (typically less than a microvolt) generated on the scalp and near the ear when a click or tone pip at the ear causes a sequence of more or less synchronized volleys of neural firings along the auditory pathway. Computer averaging has long been used for stimulus/response measurement in patients. The technique involves a) the repetitive stimulus of the patient through one or more of his nerve systems (i.e., eye, ear, touch, etc.), b) the detection of the body's response through remotely located electrodes contacting or penetrating the skin and c) the repetitive sampling or "averaging" of the detected signal in synchronism with the stimulus so as to remove the background noise that is typically many dB greater than each detected signal.

Several years ago, the applicant and others saw three unsolved problems in ABR instrumentation:

1. The electromagnetic output of traditional supra aural input headphones such as the Telephonics TDH-39 introduced an artifact into the output recording that was often impossible to separate from a real response.
2. Patient preparation included vigorous scrubbing (often resulting in lacerations) of the skin. The ABR pickup typically employed EEG electrode cups filled with silver-chloride paste, taped down over the scrubbed skin area. Several minutes were often required to prepare and apply the electrodes in order to keep the contact resistance below 5000 ohms, as was typically required in these tests.
3. Even with low-impedance electrode preparations, electrical interference from radio stations, fluorescent lights, diathermy machines and the like sometimes made it completely impossible to obtain useful ABR recordings.

The applicant has previously described insert earphones which successfully solved the first problem, specifically in U.S. Pat. No. 4,677,679 dated July 5, 1984 and U.S. Pat. No. 4,766,753 dated Oct. 4, 1985, and a low-cost earcanal electrode that has simplified the electrode preparation in many cases due to the increased signal levels resulting from electrical pickup closer to the cochlea as described in U.S. Pat. No. 4,781,196 dated Nov. 1, 1988. These patents are incorporated herein by reference and form a part of the present disclosure.

A solution to the interference problem was initially approached by attempting to locate a high-input-impedance amplifier close to the electrodes, in the belief that a lower output impedance driving the cables connecting the electrodes to the ABR equipment would alleviate the problem. After continuing failures with this approach, we built an electrically-quiet "BATMAN" (Brainstem Amplifier Test MANikin) with salty jello for brains. Tests with this manikin convinced us that our high-input-impedance electrode amplifier only indirectly tackled the real nemesis of clean bioelectric recordings: The human body acts as an efficient antenna for pickup of extraneous electromagnetic interference signals (EMI), some of which can amount to tens of volts in magnitude.

Measures taken in good ABR equipment include the use of differential input amplifiers to obtain extraordinarily high common-mode-rejection ratios and large common-mode-input voltage ranges at high frequencies. These have been brute force (and in some environments regularly unsuccessful) attempts to avoid the contamination of the averaged signal from EMI pickup. The use of light-coupled isolation amplifiers to solve this and similar problems is well known, and light-coupled amplifier-transmitter-receiver-demodulator systems are commonly available. But their power consumption and cost has hitherto prevented their common use in ABR and similar equipment.

SUMMARY OF THE INVENTION

The present invention has as its principal object the provision of an electrode amplifier that is more resistant to interference from electromagnetic noise sources.

It is a more specific object to provide an electrode amplifier that is resistant to interference from electromagnetic noise sources while being economical to manufacture and package.

It is a further object to provide an electrode amplifier that operates efficiently from a low voltage power source such as a single electrochemical cell.

It is still a further object to provide a local shielding configuration for the electrode amplifier that additionally minimizes the interference from electromagnetic noise sources.

It is also an object of the present invention to provide an electrode amplifier that is effectively transparent to existing bioelectric signal analysis equipment, so that the interference problem may be solved without requiring reprogramming or other equipment modifications.

Finally, it is a more general object of the invention to provide an improved and more economical light-coupled transmission system using pulse duration modulation.

These and other objects and advantages are provided through a system for detecting and transmitting body electrical signals in the presence of ambient electrical interference that uses a transmitter circuit including an amplifier coupled to and in close proximity to two or more body electrodes, a light pulse generator that receives its input from that amplifier and provides a pulse-duration-modulated series of light pulses, and a remote receiver including a transducer which demodulates the transmitted light pulses into electrical pulses of corresponding duration and frequency and a demodulator which accepts electrical pulses and produces an amplified replica of the original signal developed between the body electrodes, thereby effectively providing complete electrical isolation of the electrode amplifier from the remaining bioelectrical signal analysis equipment.

More specifically, these objects are accomplished in the present invention through the use of a version of the low-voltage, low-power Class D integrated circuit amplifier originally developed by the applicant for hearing aid applications (U.S. Pat. No. 4,592,087 dated May 27, 1986 and U.S. Pat. No. 4,689,819 dated Aug. 25, 1987, incorporated herein by reference to form a part of the present disclosure), in conjunction with a new voltage-doubler circuit and the unusual combination of a high-light-output fiber optic transmitter with a low-noise, low-battery-drain fiber optic receiver, and with the switching frequency of the Class D amplifier chosen so high that a four-stage passive R-C filter provides adequate filtering of the switching frequency in order to prevent unwanted interactions between it and the analog-to-digital converter in the input of the bioelectric signal equipment.

A valuable additional feature of the invention is a complete electrostatic shield around the amplifier-transmitter as well as the electrode leads, so that the small amount of residual capacitive coupling to the amplifier circuit itself is effectively shunted to the same average (body) potential as that of the electrodes.

DESCRIPTION OF THE PREFERRED EMBODIMENT

Figure 1:
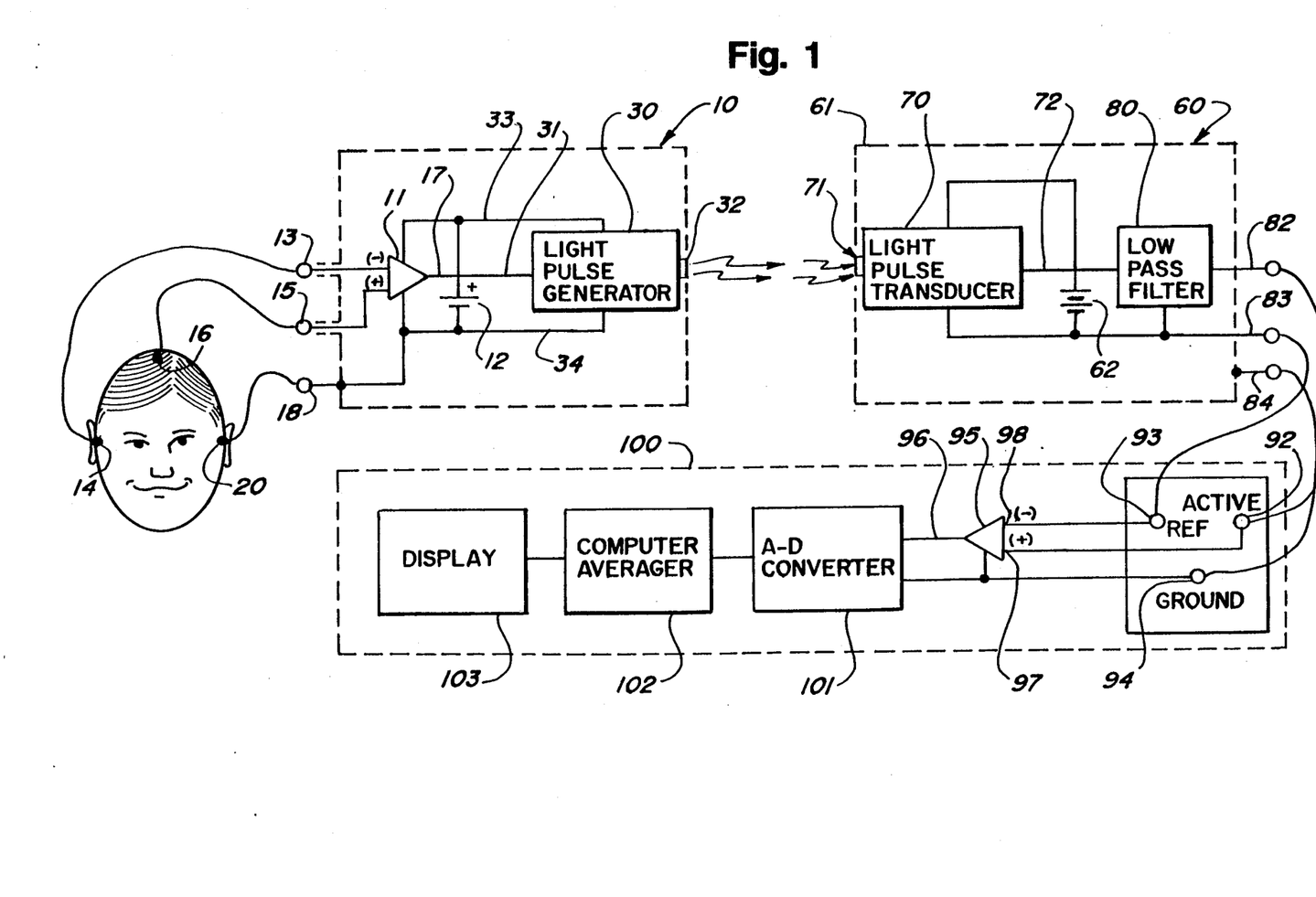
FIG. 1 is a block diagram of the transmitter and receiver system of the present invention connected between bioelectric-pickup electrodes and conventional equipment that has been designed for bioelectrical signal analysis.

Turning now to the drawings, FIG. 1 illustrates the operation of the complete inventive electrode isolation amplifier system connected to a conventional bioelectric signal analyzer. A transmitter 10 contains an electronic amplifier 11 powered by a power source 12 and having a first input 13 adapted for coupling to a first scalp-mounted electrode 14 and a second input 15 adapted for coupling to a second scalp-mounted electrode 16, and a single output 17 whose voltage amplitude is a multiple of the difference in voltage between the signals at the two electrodes 14 and 16. Electrostatic shield 19 surrounds inputs 13 and 15 and encloses the amplifier 11, power source 12 and a light pulse generator 30, and is connected to an input terminal 18 which is, in turn, connected to a "ground" electrode 20 mounted on the scalp at a distance from the two electrodes 14 and 16. The light pulse generator 30 receives at its input 31 the output of the electronic amplifier 11 and provides at its output 32 a pulsatile light whose pulse period is relatively fixed and whose pulse duration is proportional to the voltage amplitude of the output signal generated by the electronic amplifier. Both the amplifier 11 and the light pulse generator 30 are powered by the power source 12 having a positive terminal connected to a supply buss 33 and a negative terminal connected to a common buss 34.

Also shown in FIG. 1 is a receiver 60 which contains a light pulse transducer 70 with an input 71 configured to accept the transmitted light pulses from the transmitter 10 and convert them into electrical pulses at an output 72. The receiver 60 also contains a low-pass filter 80 which accepts the electrical pulses from the transducer 70 and effectively demodulates them into an amplified and isolated replica of the original voltage difference between the first and second scalp electrodes 14 and 16, which amplified replica is delivered via an active output 82 and reference output 83 to an input terminal box 90 of a bioelectric signal analysis system 100.

The bioelectric signal analysis system 100 contains a differential amplifier 95 whose non-inverting input 97 is shown connected to an input terminal 92 and whose inverting input 98 is shown connected to a reference terminal 93. A shield 61 surrounds the receiver 60 and is connected to the ground terminal 94 of the input amplifier 95, whose output 96 provides a signal to an analog-to-digital converter 101. A computer averager circuit 102 accepts the output of an A-D converter 101 and drives a suitable display 103 and/or printout. The average circuit 102 is well-known in the art and provides an output which is the averaged sum of repetitively received signals such that a principal desired pulse is amplified while surrounding noise is effectively cancelled. It is interconnected with and operates in conjunction with, and typically in synchronism with, a stimulus generator (not shown) which provides the aural input to the ear through speakers, headphones or insert earphones as described above.

Figure 2:
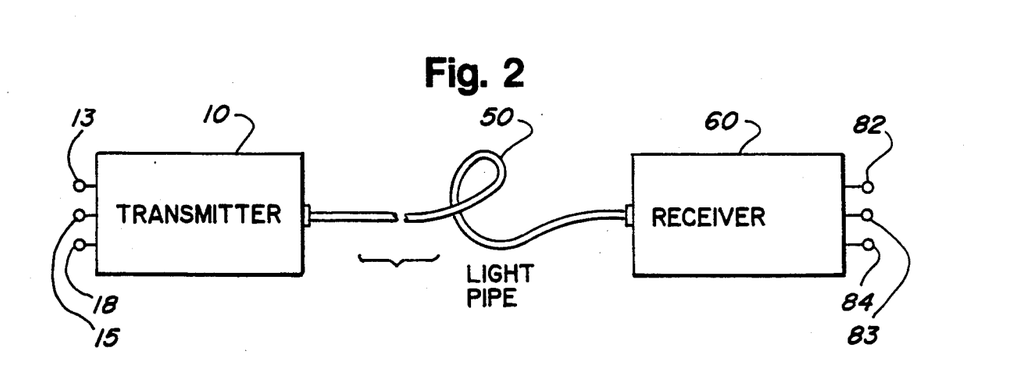
FIG. 2 is a block diagram of an embodiment of the present invention that uses a fiber optic light pipe to carry the signal.

In FIG. 1 light transmission from the output 32 to the receiver input 71 is through open space. FIG. 2 illustrates an alternative and preferred embodiment, in which a light pipe 50 connects transmitter 10 and receiver 60.

Figure 3:
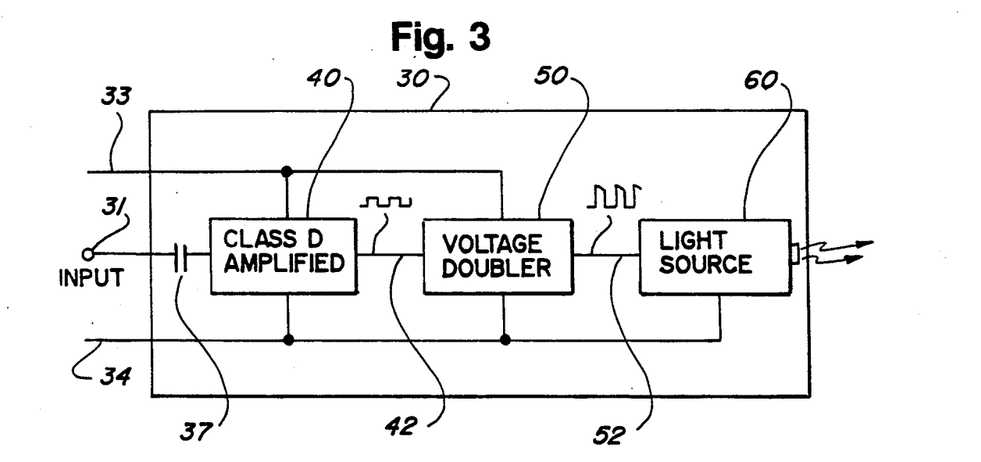
FIG. 3 is a more detailed block diagram of a portion of the transmitter shown in FIG. 1.

FIG. 3 shows a more detailed block diagram of light pulse generator 30, with an input 31 coupled through a capacitor 37 to a class D amplifier 40 whose output 42 is a square wave with duty cycle proportional to the voltage appearing between the input terminal 31 and a common terminal 34 as described in the aforementioned U.S. Pat. Nos. 4,592,087 and 4,689,819 incorporated herein by reference. The output 42 of class D amplifier 40 drives a voltage doubler 50 whose output 52 provides the greater-than-1.5 volt square wave drive required by the light-emitting diode (shown below in FIG. 4) in the preferred embodiment of the light source 60.

Figure 4:
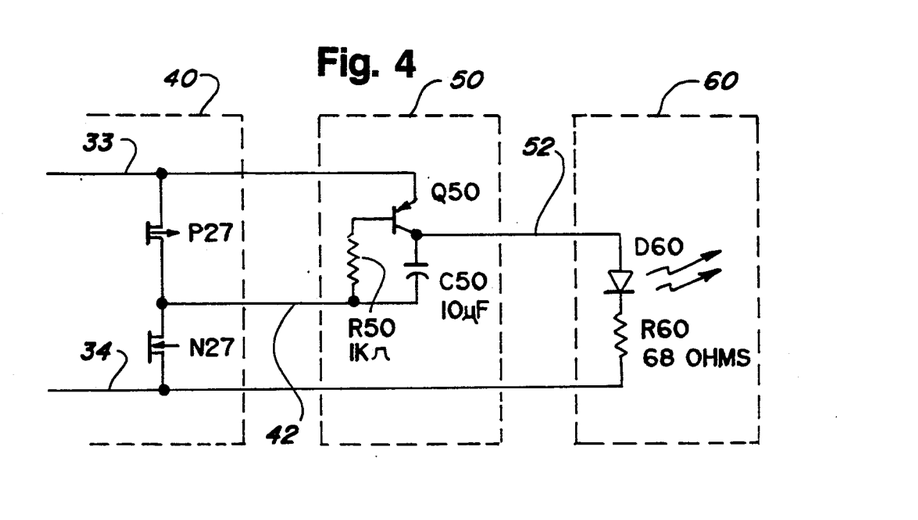
FIG. 4 is a more detailed schematic diagram of a portion of the transmitter shown in FIGS. 1 and 3.

FIG. 4 shows a schematic diagram of a preferred embodiment of parts of generator 30, where a pair of output transistors P27 and N27, as shown in FIG. 4 of and described in U.S. Pat. No. 4,689,819, supply current through a current-limiting resistor R50 to drive PNP transistor Q50 into conduction during the low-voltage output portion of the duty cycle of the Class D amplifier, thereupon charging a storage capacitor C50 to approximately 1.5 volts. On the high-voltage-output portion of the duty cycle of Class D amplifier, a voltage roughly double the supply voltage between buss 33 and common bus 34 is supplied to light source 60. The light source 60 is preferably a Thomas and Betts Model 92915-T-DD fiber optic transmitter.

Figure 5:
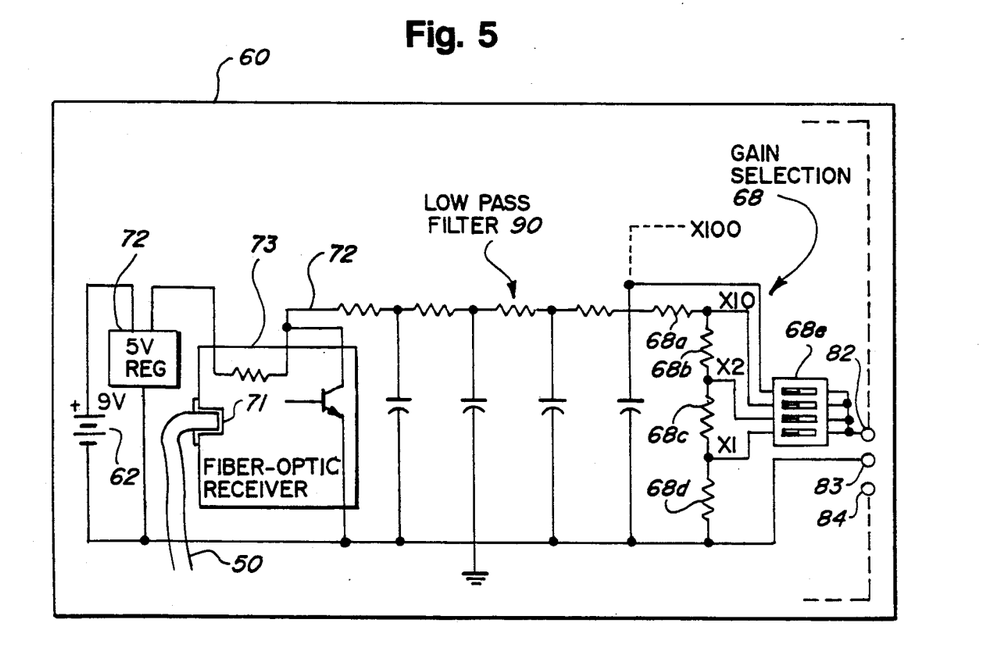
FIG. 5 is a schematic diagram of the receiver shown in FIG. 1, showing the regulator, fiber optic receiver, low pass filter, and gain selection circuit.

FIG. 5 shows a simplified schematic of the receiver 60, in which a supply 62, which may be a 9 Volt transistor radio battery, drives a regulator 72 providing 5 volts DC to the fiber optic receiver 73. Alternately, the supply 62 may be obtained from the ABR equipment itself. The fiber optic receiver 73 is preferably an hp Model 2521, whose input 71 accepts the receiver end of the fiber optic cable 50 and whose output 72 supplies an input to the low pass filter 80. By choosing the operating frequency of the class D amplifier 40 of FIG. 3 to be in the neighborhood of 300 kHz, four stages of passive R-C filtering can provide 90 dB of attenuation at the switching frequency (without significant attenuation to the desired signal in the 100 to 5000 Hz passband used for most ABR measurements). This avoids any interference with the operation of subsequent signal processing means (in the aforementioned bioelectric signal system) that might otherwise occur due to the pulsatile nature of the transmitted and received signal.

A gain selection network 68 consisting of fixed resistors 68a, 68b, 68c and 68d and a selection switch 68e is provided, permitting manually selectable overall system gains between 1× and 100×. A system gain of 1× is particularly convenient so that the operation of the inventive system appears transparent to existing sensory-electrode signal-analysis equipment except for the desired increase in resistance to disturbance from electromagnetic interference. In some situations, however, additional noise rejection can be obtained with a system gain of 2× or more.

Figure 6:
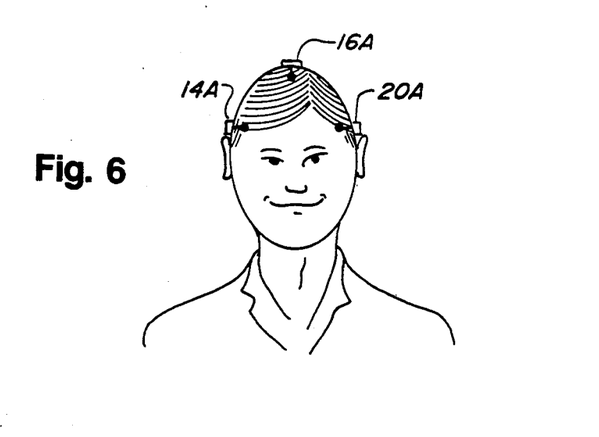
FIG. 6 is a sketch of a "BATMAN" manikin, showing the location of three of the electrodes used in the development experiments.

FIG. 6 shows a sketch of "BATMAN," a test "manikin" with electrodes 14A, 16A, and 20A formed from conventional electrode plug jacks but with a small wad of copper "Chore Girl" scrub brush on the inside of the manikin's head imbedded in a salty jello solution used to simulate an electrically quiet but normally conductive brain.

Figure 7:
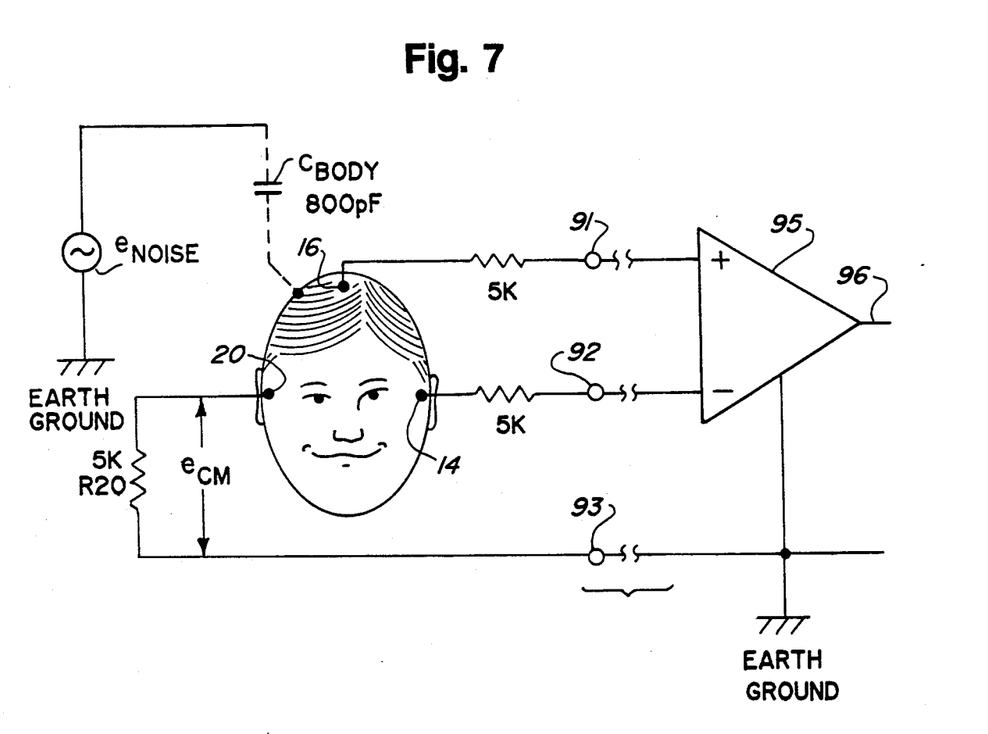
FIG. 7 is a diagram, partially in schematic form, illustrating the common-mode signal path for interfering electrostatic pickup found in conventional ABR equipment.

FIG. 7 is an equivalent circuit that illustrates the most important interference problem normally encountered, with somewhat arbitrary values of 5000 ohms shown for each electrode impedance. As is well understood, the actual impedance of a surface electrode on the skin varies with both preparation and test frequency, and only rarely do even two of the three electrodes exhibit the same impedance. The values shown are adequate for our purposes however, since only the existence of an appreciable impedance between each electrode and the "body" is required for the present explanation. Assuming an electrostatically-coupled source of noise having open circuit potential of NOISE, and taking a commonly measured capacitance from a body to "space" of about 800 pF and the assumed value of 5000 Ohms for the impedance of each electrode, it can be readily calculated that above about 40 kHz the common mode signal impressed on the inputs 91 and 92 of the conventional differential amplifier 95 is unattenuated, but equal to the open circuit value of eNOISE. When eNOISE exceeds the typical 10 volts common-mode input range of the typical operational amplifier, overload occurs and the operation of the signal averager is severely compromised. Even in the laboratory, several miles from the nearest radio stations (at 670 kHz and 720 kHz), open circuit voltages of several volts at 670 and 720 kHz were measured, indicating the severity of the problem for someone closer to such interference sources.

Figure 8A:
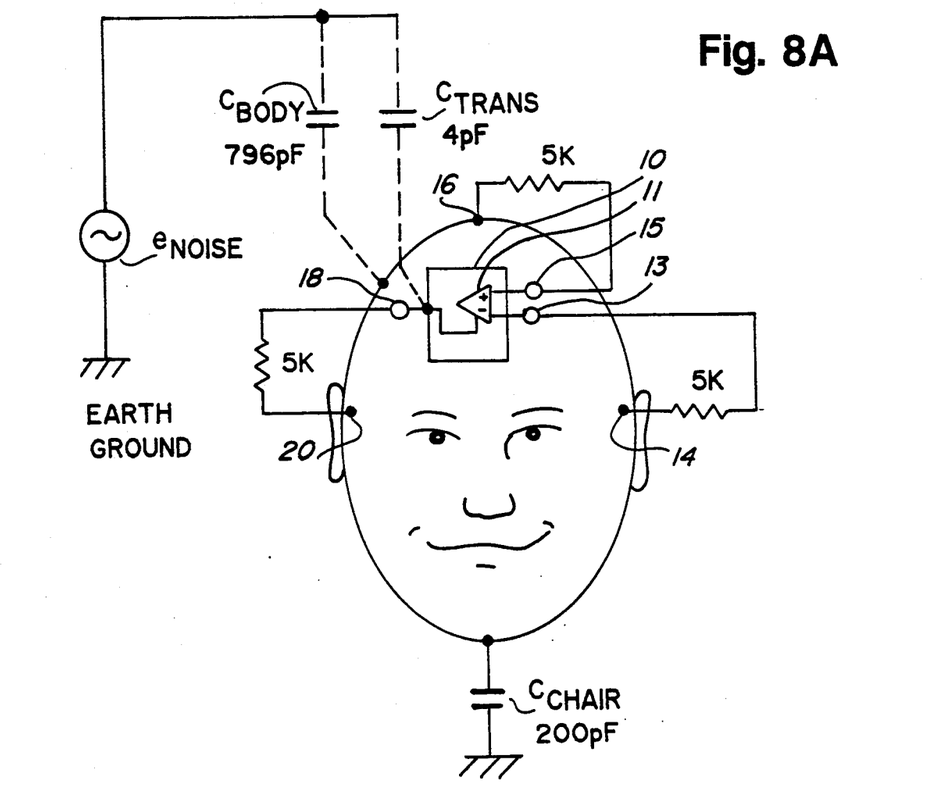
FIG. 8A is a diagram, partially in schematic form, illustrating the radically reduced common-mode signal developed at the input to the system of the present invention.

FIG. 8A shows the dramatically improved situation in which the input amplifier is mounted on or near the head in a small electrostatically shielded box, as in the present invention. Taking the surface area of a typical human as roughly 2000 square inches, and the prototype box surface area of about 10 square inches, the total coupling of roughly 800 pF is now divided into 796 pF to the head and body and 4 pF to the electrostatic shield of the transmitter box 10. If there is no capacitive coupling from the body to earth ground, there is no common mode signal developed at inputs 13 and 15 of transmitter 10, since eBODY and e18 are the same voltage. In practice, a few hundred pF of capacitance to the couch or chair in which the patient is relaxing may be expected.

Figure 8B:
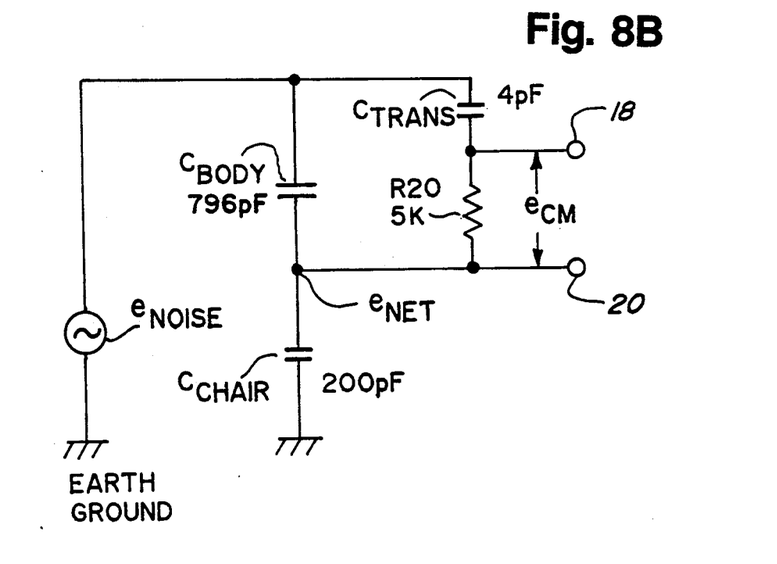
FIG. 8B is further circuit diagram, in simplified form, illustrating the nature of the residual common-mode signal developed at the input to the present invention.

FIG. 8B illustrates a further simplified circuit for the purpose of calculating the residual common mode signal when 200 pF of capacitance exists between the patient and earth ground. Even here, the common mode signal is attenuated 60 dB (0.001x) at 40 kHz and 40 dB 0.01x) at 400 kHz compared to that present at the input of differential amplifiers used in conventional ABR and other bioelectric signal equipment.

Figure 9:
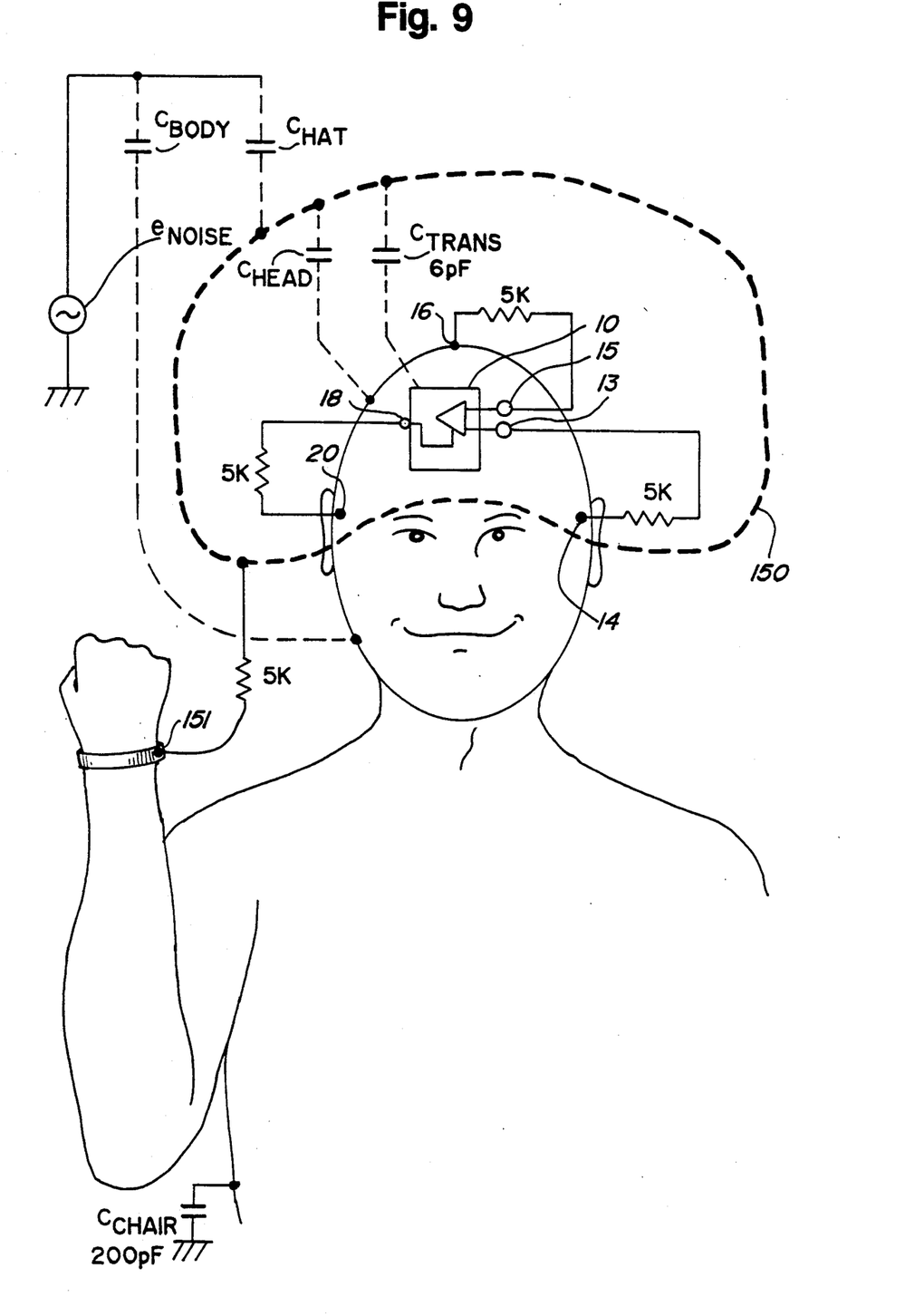
FIG. 9 is a sketch of a patient under test with a doubly-shielded isolation amplifier configuration.

FIG. 9 shows the use of an additional electrostatic shield 150, connected to a fourth electrode 151 in such a way that the primary electrostatic coupling from the source of noise voltage eNOISE is intercepted and shunted through the assumed 5 kOhm electrode impedance of electrode 151 to the patient's body. Shield 150 may take the form of a large bowl-shaped conductive shield around the head similar in shape and appearance to a hair dryer found in beauty shops. Alternately, shield 150 may be made in the form of a scarf or "babushka" woven at least partially of conductive thread such as carbonized nylon or interwoven with fine metallic strands, connected in either case to a new body electrode which may conveniently be in the form of a wrist strap. When made in the form of a scarf, shield 150 is tied around the head so that it covers the electrodes 14, 16, and 20 and the transmitter 10. (With appropriate choice of colors, these electrostatic shields might even become important fashion statements among chronic ABR patients, but no such claim is made here.)

It is readily seen that with the shield 150 in place, the majority of the capacitively induced current that would otherwise develop a common mode voltage at terminal 18 is shunted to the body through electrode 151, providing a further 20 to 40 dB improvement in interference rejection.

The dramatic reduction in common mode voltage provided by the shielding configuration of FIGS. 8a and 8b permits a simple "single-ended" input design for the input amplifier 11 of FIG. 1, provided that a balance in circuit-to-shield capacitance is maintained for inputs 13 and 15.

In particular, a simple "single-ended input" amplifier effectively becomes, in this light-coupled, electrostatically-shielded configuration, a differential amplifier with extraordinarily high common mode rejection ratio: A measured improvement of some 26 dB in interference rejection is obtained over the best-quality conventional bioelectric-pickup differential amplifiers. Indeed, clean ABR recordings can be achieved with the inventive amplifier even while the patient under test is grasping an active desk-type fluorescent light fixture and bulb: a source of interference that typically overloads the high-quality conventional ABR equipment by a factor of 10 to 20 times, preventing any interpretable readout.

Since interference pickup is proportional to the size of the surface area of the transmitter assembly and its optional electrostatic shield, operation is enhanced in the present embodiment by the availability of the aforementioned self-contained class D amplifier integrated circuit chip measuring approximately 2 mm by 1 mm by 0.3 mm thick (the light emitting diode element in the transmitter can be of similar dimensions), which permits an unusually small size for such a transmitter package. Similarly, the high efficiency of that class D amplifier and its proper operation with supply voltages as low as 1.1 volts means that a miniature hearing-aid size single-cell "battery" can provide adequate power while maintaining a small size for the overall package. The complete transmitter can be operated from a single-cell "675" size hearing aid battery with a current drain of only 5-10 mA, permitting 40 hours or more of operation before battery replacement is required, at a cost of only a few cents per hour of operation: a trivial cost when compared to the typically $100 to $200 per hour that is charged for ABR measurements. One successful measurement that would otherwise have been lost to interference would pay for batteries for several thousand complete ABR measurements.

I claim as my invention:

1. A system for detecting and transmitting body electrical signals in the presence of ambient electrical interference, comprising:
   at least two electrodes adapted for attachment to the body at spaced body locations between which electrical signals are generated by the body in response to a predetermined stimulus;
   an independently-grounded transmitter circuit arranged to be mounted in close proximity to and attachable to the body and coupled to said electrodes in close proximity thereto, said circuit comprising:
   a) a source of electrical power;
   b) amplifier means coupled to said source for energization therefrom and having an input arranged to be coupled to said electrodes to detect body signals and operative for developing an output signal whose magnitude varies with the detected body signals;
   c) light pulse generator means coupled to said amplifier to respond to said output signal and to develop output light pulses having durations which vary in accordance with said amplifier output signal; and
   d) grounding means for providing independent ground path of short length between the body and said source and said amplifier means to minimize electrical interference;
   a receiver optically coupled to and remote from said transmitter and comprising:
   a) a transducer converting said transmitted light pulses into electrical pulses of corresponding duration and frequency, and
   b) demodulation means responsive to said transducer electrical pulses and producing an amplified version of the original signal between said first and second electrodes, said electrical power source being a minature single-cell battery, said light pulse generator including a light emitting diode and a voltage doubler circuit connected to said single-cell battery and driven from said amplifier output signal, said voltage doubler circuit being arranged for supplying voltage pulses to said diode at an amplitude level substantially greater than the voltage available from said single-cell battery.

* * * * *